US008882733B2

(12) United States Patent
Rodrigue et al.

(10) Patent No.: US 8,882,733 B2
(45) Date of Patent: Nov. 11, 2014

(54) DIAPER FOR TREATMENT OF DIAPER RASH AND METHODS OF USING SUCH A DIAPER

(71) Applicants: Anna Maria Rodrigue, Los Angeles, CA (US); Adam Tyler, Los Angeles, CA (US)

(72) Inventors: Anna Maria Rodrigue, Los Angeles, CA (US); Adam Tyler, Los Angeles, CA (US)

( * ) Notice: Subject to any disclaimer, the term of this patent is extended or adjusted under 35 U.S.C. 154(b) by 0 days.

(21) Appl. No.: 13/655,327

(22) Filed: Oct. 18, 2012

(65) Prior Publication Data

US 2014/0114270 A1   Apr. 24, 2014

(51) Int. Cl.
*A61F 13/15* (2006.01)

(52) U.S. Cl.
USPC ............ 604/385.01; 604/385.09; 604/385.11; 604/385.14; 604/385.19; 604/389; 604/395

(58) Field of Classification Search
USPC ............... 604/385.01, 389, 395, 397, 385.09, 604/385.14, 385.11, 385.19
See application file for complete search history.

(56) References Cited

U.S. PATENT DOCUMENTS

| 1,033,235 | A | 7/1912 | Eshborn |
| 1,695,109 | A | 12/1928 | Kosloff |
| 2,024,341 | A | 12/1935 | De Graff |
| 2,837,095 | A | 6/1958 | Stevenson |
| 3,616,798 | A | 11/1971 | Garfinkel |
| 4,229,835 | A | 10/1980 | Shaw |
| 4,951,321 | A | 8/1990 | Mortensen et al. |
| 5,137,525 | A | * 8/1992 | Glassman ................ 604/385.11 |
| 5,207,663 | A | 5/1993 | McQueen |
| 5,239,706 | A | 8/1993 | Stevenson |
| 5,549,775 | A | 8/1996 | Odorzynski |
| 5,810,797 | A | 9/1998 | Menard et al. |
| 6,102,899 | A | 8/2000 | Yimin |
| 6,152,906 | A | 11/2000 | Faulks et al. |
| 6,817,991 | B1 | 11/2004 | Jabalee |
| 6,932,800 | B2 | 8/2005 | LaVon et al. |
| 6,989,005 | B1 | 1/2006 | LaVon et al. |
| 7,716,753 | B2 | 5/2010 | Franko |
| 2007/0130671 | A1 | 6/2007 | Solomon |
| 2008/0229487 | A1 | 9/2008 | Kweon |

FOREIGN PATENT DOCUMENTS

| GB | 02042342 A | 9/1980 |
| JP | 10-085275 A | 4/1998 |
| WO | WO-01/24753 A1 | 4/2001 |

* cited by examiner

*Primary Examiner* — Jacqueline F. Stephens
(74) *Attorney, Agent, or Firm* — Venable LLP; Michael A. Sartori

(57) ABSTRACT

A diaper for treatment of diaper rash and methods of using such a diaper to treat diaper rash are provided. The diaper may include a first layer having inner and outer surfaces and including a front portion, a rear portion, and a middle portion extending between the front and rear portions and configured to be positioned between the legs of a user when worn. A liquid absorbent element may be coupled to the inner surface of the first layer and disposed proximate at least the front and middle portions. An opening may be defined in the rear portion of the first layer to expose at least a portion of the user's buttocks to open air when worn. An air and liquid permeable mesh layer may be permanently or removeably attached adjacent the opening and may cover at least part of the opening.

17 Claims, 5 Drawing Sheets

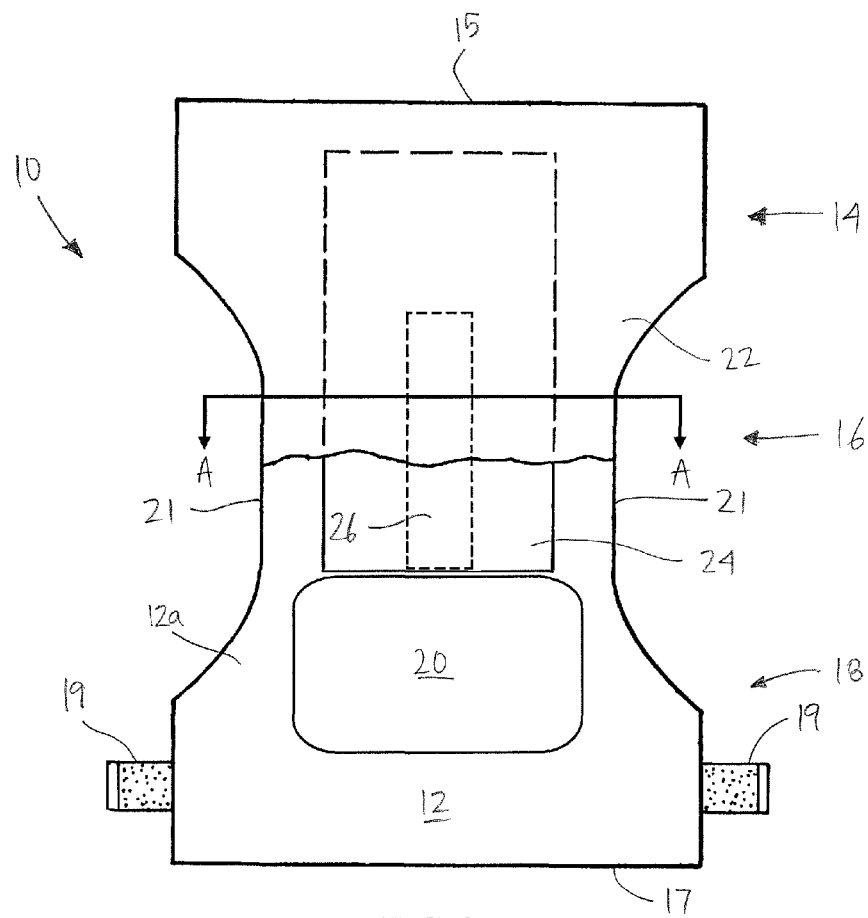
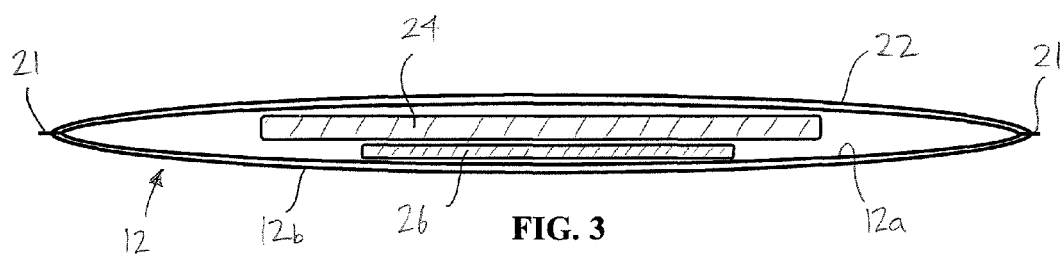
FIG. 2
FIG. 3

DIAPER FOR TREATMENT OF DIAPER RASH AND METHODS OF USING SUCH A DIAPER

BACKGROUND

1. Field of Invention

The invention relates generally to a diaper and, more particularly, to a diaper for the treatment of diaper rash and methods of using such a diaper.

2. Related Art

Irritant diaper dermatitis (IDD), commonly known as "diaper rash," is a common skin problem that develops in the area beneath an infant's or toddler's diaper. Diaper rash is typically caused by prolonged exposure to wetness (especially urine and feces), which results in increased skin pH and the deterioration of the outermost layer of the skin (i.e., stratum corneum). Moisture-absorbing powders and protective ointments, jellies, and creams are often helpful both in prevention and as recommended remedies, but often do not ultimately treat the affliction in a timely manner and, in some cases, can actually worsen the condition.

Baby experts and pediatricians have often suggested exposing the affected area to air as an effective treatment for diaper rash. Air exposure, especially if prolonged, can often heal diaper rash many times faster than using a cream, ointment or other similar topical remedies. Removing a baby's diaper for any significant period of time, however, can be a messy proposition due to the frequency of urination by infants and/or toddlers. Many mothers, for example, often resort to placing infants on their stomachs on a protective cloth configured to absorb urine. While this might be viable for very young infants who are effectively immobile, it can be difficult for older infants and toddlers due to the inherent difficulty in keeping the child stationary for any length of time.

What is needed is a low cost, easy-to-use product for the temporary treatment of diaper rash that allows areas affected by diaper rash to receive air exposure while still providing a non-potty-trained infant or toddler with a measure of protection in the event of sudden urination and/or a bowel movement.

SUMMARY

In accordance with an embodiment of the invention, a diaper for treatment of diaper rash is provided. The diaper may include a first layer having inner and outer surfaces and including a front portion, a rear portion, and a middle portion extending between the front and rear portions and configured to be positioned between the legs of a user when worn. A liquid absorbent element may be coupled to the inner surface of the first layer and disposed proximate at least the front and middle portions. An opening may be defined in the rear portion of the first layer to expose at least a portion of the user's buttocks to open air when worn. An air and liquid permeable mesh layer may be permanently or removeably attached adjacent the opening and may cover at least part of the opening.

According to another embodiment of the invention, a method for using a diaper to treat diaper rash may be provided. The method may include providing the diaper and removably securing the diaper to an infant or toddler with diaper rash. When secured on the infant or toddler, a front portion of the diaper may contact a front hypogastric region and may cover the genitalia of the infant or toddler. The rear portion may contact a lower lumbar region and may cover the buttocks of the infant or toddler. The middle portion may extend between the legs of the infant or toddler. The opening having the air and liquid permeable mesh layer covering at least a portion thereof may expose at least a portion of the infant's or toddler's buttocks to open air for treatment of diaper rash.

Further features and advantages, as well as the structure and operation of various embodiments of the invention, are described in detail below with reference to the accompanying drawings.

BRIEF DESCRIPTION OF THE DRAWINGS

The foregoing and other features and advantages of the invention will be apparent from the following, more particular description of some embodiments of the invention, as illustrated in the accompanying drawings. Unless otherwise indicated, the accompanying drawing figures are not to scale. Several embodiments of the invention will be described with respect to the following drawings, in which like reference numerals represent like features throughout the figures, and in which:

FIG. 2 is a schematic top view of the diaper depicted in FIG. 1;

FIG. 3 is a schematic cross-sectional view of the diaper of FIG. 2 taken along line A-A;

DETAILED DESCRIPTION

Some embodiments of the invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the invention.

Figure 1:
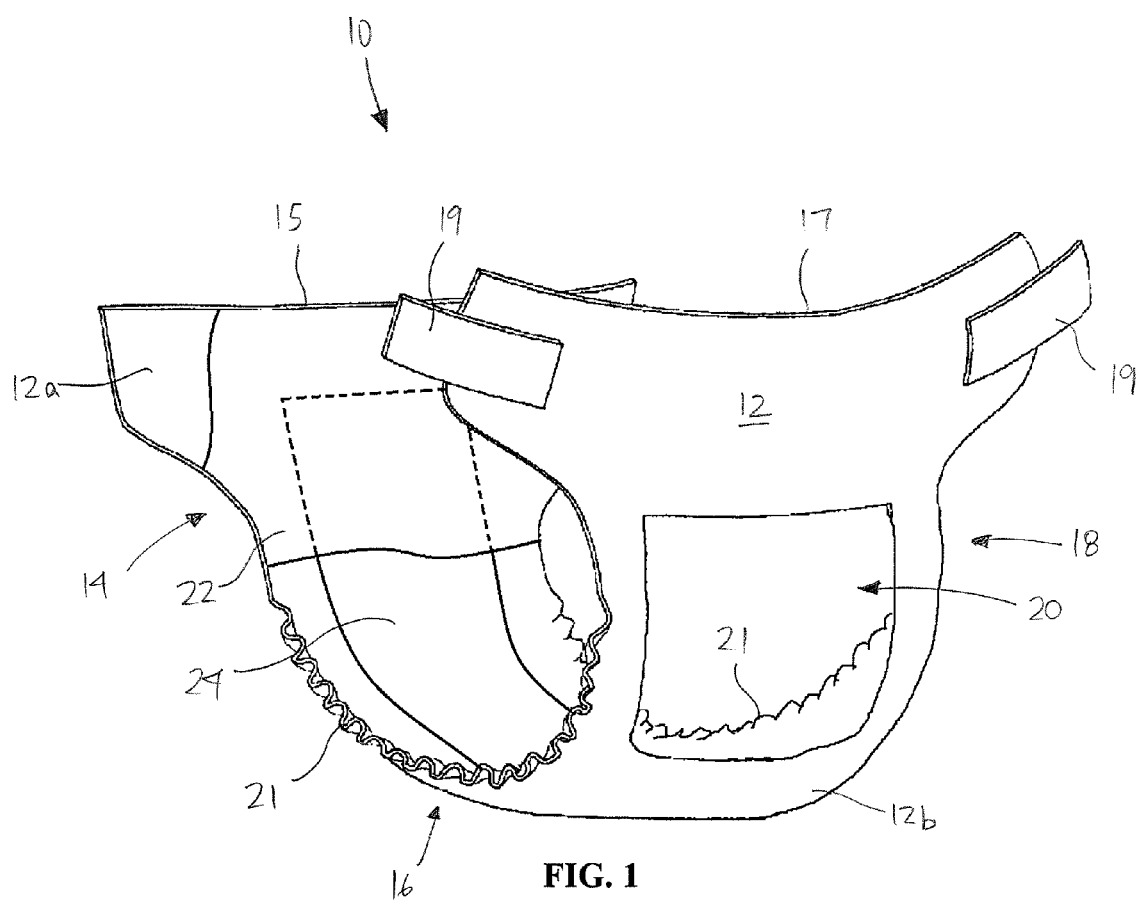
FIG. 1 is a schematic rear perspective view of a diaper for treating diaper rash according to an embodiment of the invention.

FIG. 1 is a schematic rear perspective view of a diaper 10 for treating diaper rash according to an embodiment of the invention. FIG. 2 is a schematic top view of the diaper 10. As shown in FIGS. 1 and 2, the diaper 10 may be a disposable diaper or a reusable diaper such as, for example, a cloth diaper or a pocket diaper for use with cloth diapers. The diaper 10 may include, for example, an outer sheet or layer 12 defining an inner surface 12a and an outer surface 12b. The layer 12 may be a liquid impermeable material and may include a front portion 14, a middle portion 16, and a rear portion 18. The front and rear portions 14, 18 may include waist band portions 15, 17, respectively, one or both of which may include elastic material (not shown) to provide a comfortable, snug, and flexible fit around the waist of the user such as, for example, an infant or toddler. The waist band portions 15, 17 may form a continuous waist band such as utilized, for example, in a training ("pull-up") diaper or they may be configured as opposite ends of a conventional diaper arranged to be manually and removeably connected to one another around the waist of the user. As shown in FIG. 1, the rear waistband portion 17 may include attachment strips 19 arranged at the outer edges thereof for attachment to the outer surface 12b of the front portion 14. The attachment strips 19 may include adhesive tabs, hook-and-loop fasteners, snaps, buttons, or other known removably attachable fastening elements as will be readily apparent to one having ordinary skill in the pertinent art. The peripheral side edges of the contoured middle portion 16 may include elastic material 21 to provide a comfortable, snug, and flexible fit around the legs of the infant or toddler when worn. The diaper 10 may include an opening 20 centrally defined in the rear portion 18 between the rear waistband 17 and the middle portion 16. The opening 20 may be provided and positioned to allow sufficient airflow to the areas most commonly affected by diaper rash (i.e., the buttocks and anus of the user). While the opening 20 depicting in FIGS. 1 and 2 is shown as substantially rectangular, the opening 20 may be any shape and could include more than one opening of the same or different sizes so long at it provides sufficient airflow to the buttocks and anus of the user. Additionally, the diaper 10 may include an inner liquid permeable layer 22 coupled to the inner surface 12a of the outer sheet or layer 12 and an absorbent layer or element 24 provided between the inner layer 22 and the outer layer 12. The absorbent element 24 may include one or more such elements and may be positioned in at least the front and middle portions 14, 16 of the diaper 10. The absorbent element 24 may also be formed from any known material to absorb and hold liquid and moisture.

FIG. 3 is a schematic cross-sectional view of the diaper of FIG. 2 taken along line A-A. As shown in the embodiment depicted in FIGS. 2 and 3, the inner liquid permeable layer 22 may be coupled to the inner surface 12a of the outer sheet or layer 12 and the absorbent element 24 may be provided between the inner layer 22 and the outer layer 12. A support element 26 may also be provided to maintain a contoured shape of the middle portion 16. That is, due to the opening 20, the middle portion 16 may not be sufficiently supported to maintain its shape, particularly when the diaper 10 is soiled with urine and/or feces by the infant or toddler wearing the diaper 10. In the embodiment depicted, the support element 26 is schematically shown in the form of an elongated, contoured plate which extends through the middle portion 16 of the diaper 10 up to, for example, a bottom edge of the opening 20. The support element 26 may include one or more such plates or may also be in the form of one or more elongated rods disposed in the middle portion 16 of the diaper 10. When in the form of a plate or rod, the support element 26 could be formed from any suitable material such as, for example but not limited to, metal, plastics such as PVC- and/or polyurethane-based plastics, wood, textile material, fabric material, reinforced fabric material, fabric and bonding agent composite material, composite material, and combinations thereof. As shown in the cross-sectional view depicted in FIG. 3, the support element 26 may be disposed centrally and positioned, for example, between the absorbent element 24 and the inner surface 12a of the outer layer 12. Although not shown, support element 26 could also be, for example, disposed within absorbent element 24 or on the exterior of outer surface 12b.

Upon removably securing the diaper 10 to an infant or toddler with diaper rash, the front portion 14 may contact a front hypogastric region and cover the genitalia of the infant or toddler. The rear portion 18 may contact a lower lumbar region and at least partially covers the buttocks of the infant or toddler. The middle portion 16 extends between the legs of the infant or toddler. The opening 20 may expose at least a portion of the user's buttocks and anus to open air for treatment of diaper rash.

Figure 4:
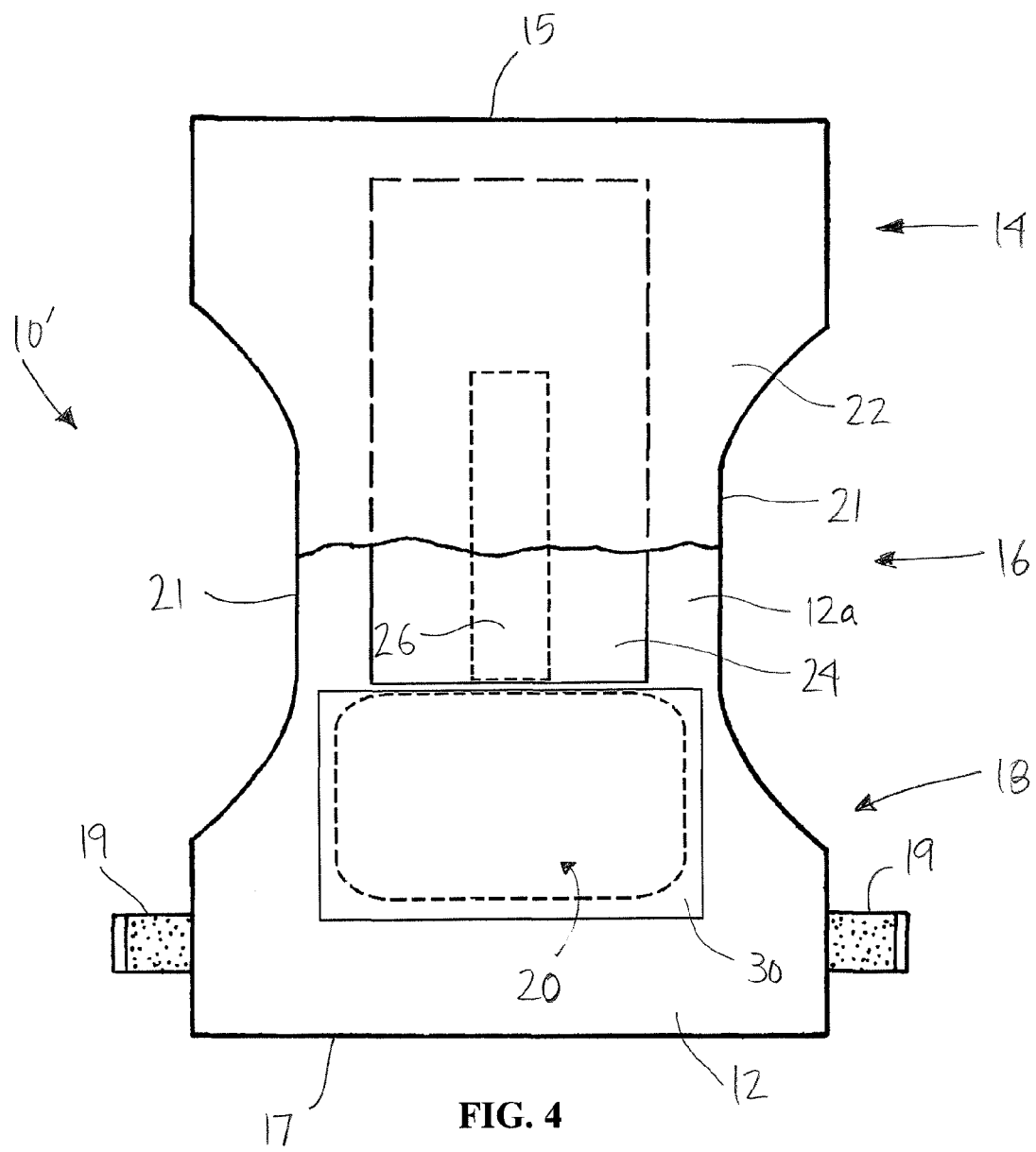
FIG. 4 is a schematic top view of a diaper for treating diaper rash according to another embodiment of the invention.

FIG. 4 is a schematic top view of a diaper 10' for treating diaper rash according to another embodiment of the invention. The diaper 10' is substantially identical to the diaper 10 described above with regard to FIGS. 1-3, except that an air and liquid permeable mesh layer 30 is provided covering at least part of the opening 20 defined in the rear portion 18 of the outer layer 12. The mesh layer 30 may be attached (removably or permanently) to the inner surface 12a, between the inner and outer surfaces 12a, 12b, or to the outer surface 12b of the layer 12 and may allow airflow therethrough to the user's buttocks and anus for treatment of diaper rash. The mesh layer 30 may be used concurrently with the support element 26 as described above or, alternatively, may itself serve as the support element in that attachment of the mesh layer 30 between the top and bottom edges of opening 30 may sufficiently support the middle portion 16 to maintain its shape, particularly when the diaper 10' is soiled with urine and/or feces by the infant or toddler wearing the diaper 10'. The mesh layer 30 may be formed from any air and liquid permeable material such as, for example but not limited to, one or more layers of plastic material, fabric material (including animal, plant, mineral, and/or synthetic), polymers, and combinations thereof and may be knit, woven, or unwoven.

While not shown, other elements capable of supporting the middle portion 16 while allowing sufficient airflow through opening 20 are envisioned including features extending across the opening 20 between the rear waistband 17 and the lower edge of opening 20 such as, for example, at least one thread element extending from a top of the opening 20 to a bottom of the opening 20.

Figure 5:
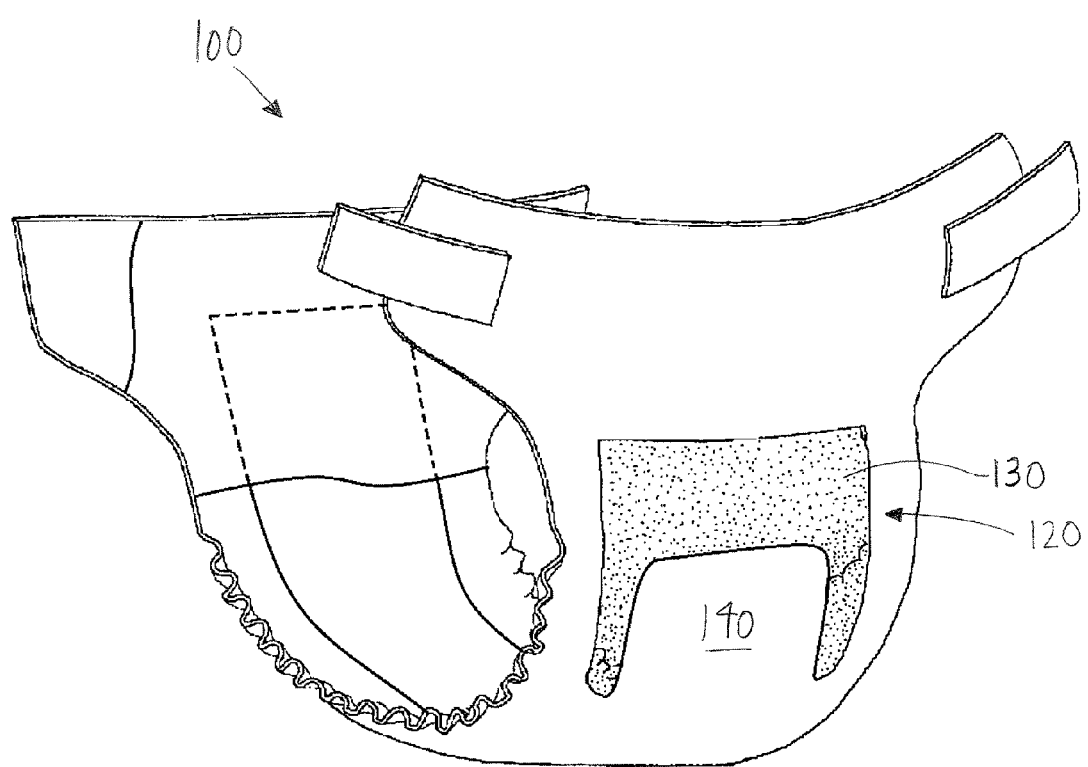
FIG. 5 is a schematic rear perspective view of a diaper for treating diaper rash according to another embodiment of the invention.
Figure 6:
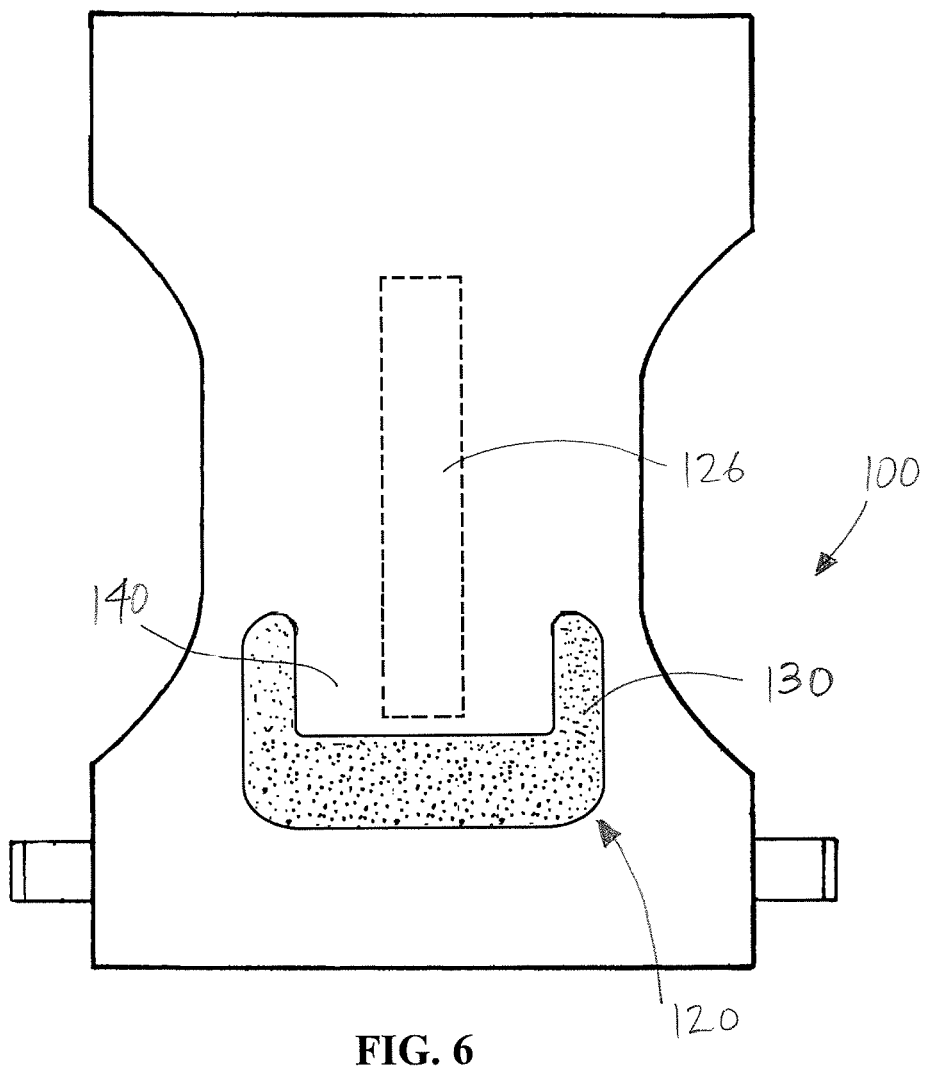
FIG. 6 is a schematic top view of the diaper depicted in FIG. 5.

FIG. 5 is a schematic rear perspective view of a diaper 100 for treating diaper rash according to an embodiment of the invention. The diaper 100 is substantially identical to the diapers 10 and 10' described above with regard to FIGS. 1-4, except that, in addition to an air and liquid permeable mesh layer 130 covering at least part of the opening 120 defined in the rear portion of the diaper 100, a contoured extension portion 140 may extend from a bottom edge of the opening 120 to cover a lower portion of the opening 120 and ensure that feces is retained within the diaper. FIG. 6 is a schematic top view of the diaper 100 of FIG. 5. As shown in FIG. 6, a support element 126 may also be provided to maintain a contoured shape of the middle portion of the diaper 100 and arranged to support the extension portion 140.

While various embodiments of the present invention have been described herein, it should be understood that they have been presented by way of example only, and not limitation. Thus, the breadth and scope of the present invention should not be limited by any of the described embodiments, but should instead be defined only in accordance with the following claims and their equivalents.

What is claimed is:

1. A diaper for treatment of diaper rash, comprising:
 a first layer having inner and outer surfaces and including:
  a front portion;
  a rear portion; and
  a middle portion extending between the front and rear portions and configured to be positioned between the legs of a user when worn;
 a liquid absorbent element coupled to the inner surface of the first layer and disposed proximate at least the front and middle portions;
 an opening defined through the rear portion of the first layer to expose at least a portion of the user's buttocks to open air when worn; and
 an air and liquid permeable mesh layer attached adjacent the opening and covering at least part of the opening.

2. The diaper according to claim 1, wherein the first layer comprises a liquid impermeable material.

3. The diaper according to claim 2, further comprising a liquid permeable second layer coupled to the inner surface of the first layer in at least the front and middle portions.

4. The diaper according to claim 3, wherein the liquid absorbent element is disposed between the first and second layers.

5. The diaper according to claim 1, further comprising a support element comprising at least one contoured plate or rod coupled to the inner surface of the first layer, an end of the support element provided proximate an edge of the opening in the rear portion.

6. The diaper according to claim 5, wherein the plate or rod is made of a semi-rigid material selected from the group consisting of metal, plastic, wood, textile material, fabric material, a composite, and combinations thereof.

7. The diaper according to claim 1, wherein the mesh layer comprises a knit, woven, or unwoven material selected from the group consisting of a plastic material, a fabric material, and combinations thereof.

8. A method for using a diaper to treat diaper rash, comprising:
   providing the diaper according to claim 1;
   removably securing the diaper to an infant or toddler with diaper rash, wherein the front portion contacts a front hypogastric region and covers the genitalia of the infant or toddler, the rear portion contacts a lower lumbar region and covers the buttocks of the infant or toddler, and the middle portion extends between the legs of the infant or toddler, and wherein the opening exposes at least a portion of the buttocks to open air.

9. The diaper according to claim 1, wherein the air and liquid permeable mesh layer is a different material than a material of the rear portion of the first layer.

10. The diaper according to claim 1, wherein the air and liquid permeable mesh layer is permanently attached adjacent the opening.

11. The diaper according to claim 1, wherein the air and liquid permeable mesh layer is removeably attached adjacent the opening.

12. The diaper according to claim 1, wherein the air and liquid permeable mesh layer covers the entire opening.

13. The diaper according to claim 1, wherein the opening is wider than the liquid absorbent element.

14. The diaper according to claim 1, wherein the rear portion comprises an end portion from an edge of the opening to an edge of the diaper, wherein a width of the opening is greater than a width of the end portion.

15. The diaper according to claim 1, wherein the first layer includes an extension portion extending into the opening.

16. The diaper according to claim 15, wherein a width of the extension portion is less than a width of the opening.

17. The diaper according to claim 15, further comprising a support element to maintain a contoured shape of the middle portion and to support the extension portion.

* * * * *